US009414898B2

(12) United States Patent
Bederak

(10) Patent No.: US 9,414,898 B2
(45) Date of Patent: Aug. 16, 2016

(54) DENTAL IMPLANTS—REPLICAS OF CUSTOMIZED ABUTMENT AND IMPLANT ANALOGS

(71) Applicant: Lev Bederak, Kiryat Motzkin (IL)

(72) Inventor: Lev Bederak, Kiryat Motzkin (IL)

(73) Assignee: ANALOYD LTD., Haifa (IL)

(*) Notice: Subject to any disclaimer, the term of this patent is extended or adjusted under 35 U.S.C. 154(b) by 61 days.

(21) Appl. No.: 14/183,280

(22) Filed: Feb. 18, 2014

(65) Prior Publication Data

US 2015/0230897 A1 Aug. 20, 2015

(51) Int. Cl.
*A61C 8/00* (2006.01)
*A61C 13/34* (2006.01)

(52) U.S. Cl.
CPC ............... *A61C 13/34* (2013.01); *A61C 8/0001* (2013.01)

(58) Field of Classification Search
CPC ....... A61C 8/0001; A61C 13/34; A61C 13/08
USPC ............................................ 433/74, 213, 214
See application file for complete search history.

(56) References Cited

U.S. PATENT DOCUMENTS

| | | | | |
|---|---|---|---|---|
| 4,622,011 A * | 11/1986 | Malek | ............................ | 433/221 |
| 5,052,929 A * | 10/1991 | Seal | ........................ | A61C 8/005 433/173 |
| 5,658,147 A * | 8/1997 | Phimmasone | ................. | 433/213 |
| 5,681,167 A * | 10/1997 | Lazarof | ................ | A61C 8/0001 433/173 |
| 5,762,500 A * | 6/1998 | Lazarof | ................ | A61C 8/0001 433/173 |
| 5,904,483 A * | 5/1999 | Wade | .................... | A61C 8/0048 433/173 |
| 5,934,906 A * | 8/1999 | Phimmasone | ................. | 433/172 |
| 6,358,052 B1 * | 3/2002 | Lustig et al. | .......... | A61C 8/0001 433/174 |
| 6,478,580 B1 * | 11/2002 | Silva | ................................ | 433/74 |
| 6,951,460 B2 | 10/2005 | Halldin et al. | | |
| 7,922,488 B2 * | 4/2011 | Falk et al. | ........... | A61C 13/0001 433/173 |
| 8,628,327 B1 * | 1/2014 | Blaisdell et al. | ............... | 433/213 |
| 2002/0049009 A1 | 4/2002 | Rabenstein | | |
| 2009/0081613 A1 * | 3/2009 | Ihde et al. | ...................... | 433/173 |
| 2011/0294093 A1 * | 12/2011 | Herweg et al. | ................. | 433/172 |

* cited by examiner

*Primary Examiner* — Ralph Lewis
(74) *Attorney, Agent, or Firm* — Mark David Torche; Patwrite LLC

(57) ABSTRACT

A method of preparing a dental prosthesis to be attached onto a dental implant. A replica including at least a segment of a customized abutment substitutes the customized abutment for supporting the dental prosthesis while it is being installed onto the physical model for its processing. An improved implant analog and the replica of the customized abutment are provided as well.

4 Claims, 2 Drawing Sheets

DENTAL IMPLANTS—REPLICAS OF CUSTOMIZED ABUTMENT AND IMPLANT ANALOGS

CROSS REFERENCE TO RELATED APPLICATIONS

None.

FIELD OF THE INVENTION

The present invention relates in general to dental implants, in particular to a system including a dental implant, a customized abutment, an implant analog that is removably attached to a physical model of the mouth of a patient, and a replica of the customized abutment and of the implant analog.

BACKGROUND OF THE INVENTION

It is well known that repeatedly removing and inserting back an abutment into a dental implant which is already placed within the jaw of a patient may harm the crest of the alveolar bone and is associated with a risk of injuring and contaminating the treated area, and interfering with the healing of the bone and surrounding gum.

SUMMARY OF THE INVENTION

A method of preparing a dental prosthesis to be attached onto a dental implant. A replica including at least a segment of a customized abutment substitutes the customized abutment for supporting the dental prosthesis while it is being installed onto the physical model for its processing. An improved implant analog and the replica of the customized abutment are provided as well.

Other features and advantages of the instant invention will become apparent from the following description of the invention which refers to the accompanying drawings.

DETAILED DESCRIPTION OF THE INVENTION

In accordance with the present invention a dental system to be used by care providers for processing a dental prosthesis, while carrying out a dental restoration, is provided. A dental system of the invention includes an improved implant analog and a replica of a customized abutment mounted therein. Additionally, according to a preferred embodiment of the method of the present invention a replica of this implant analog out of which a segment of a replica of the respective customized abutment protrudes, is provided as well. Systems of the invention provide for completing a dental restoration process in which the need to remove a customized abutment off a respective implant is practically avoided. The systems of the invention enable accomplishing an entire dental restoration process up to its final stage without releasing and/or removing the customized abutment off the respective implant.

Furthermore, means for fast connecting/releasing the implant analog of the invention, to, or off, the respective physical model of the mouth of the patient make the processing of the dental prosthesis less cumbersome, tiresome and easy to operate. Thereby the dental restoration process considered can be substantially improved; the work of the technician can become more efficient, and less expensive.

Figure 1A:
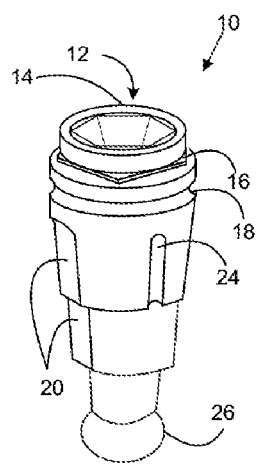
FIG. 1A is an isometric view of a dental implant analog according to a preferred embodiment of the present invention.
Figure 1B:
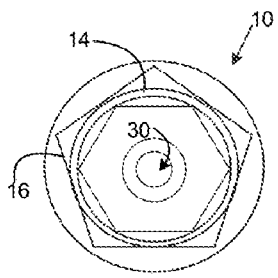
FIG. 1B is an elevational view of the side including the face of the implant analog shown in FIG. 1A.
Figure 1C:
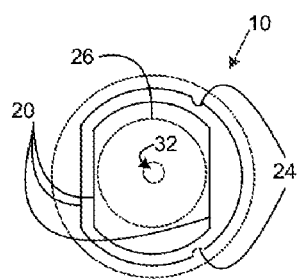
FIG. 1C is an elevational view of the side of the implant analog shown in FIG. 1A which opposes the side shown in FIG. 1B.
Figure 2A:
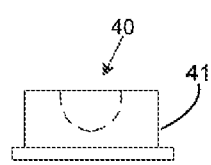
FIGS. 2A-2B are two different elevational views of an exemplary retention member providing for fixing the implant analog secured to the base of a physical model of the mouth of a patient.
Figure 2B:
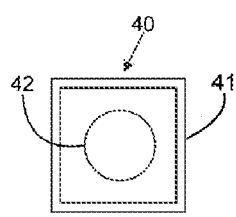

Reference is first made to FIGS. 1-2B. In FIGS. 1A-1C an isometric view and two elevational views of improved implant analog 10, which is in accordance with a preferred embodiment of the present invention, are respectively shown. (In FIGS. 1A-1C the same parts of improved implant analog 10 are designated with the same numbers.) The internal surface of the outermost segment of bore 12 need not necessarily be hexagonally shaped, as shown. However, the geometrical shape of this surface is in accordance with the geometrical shape of the respective keying, or orienting surfaces of the abutment to be introduced into the implant considered. Bore 12 has a circular rim, which is referred hereinafter as face 14 of implant analog 10. Improved implant analog 10 can be oriented in any direction in space. However for better describing and explaining the features of the improved implant analog of the invention, the side in which face 14 is located is referred hereinafter as the upper side. Pentagon 16, which is circumferential to face 14, is placed closely below face 14. Pentagon 16 provides for axially orienting a replica of the abutment that is recombined of fragments of a broken replica (such as typically occurs in cases in which the technician tries to fix a broken replica instead of casting a new one). The inner surface of bore 12 is suitably threaded, not shown, such that the abutment considered and/or a replica of the abutment as described infra, can be screwed and firmly secured into the implant analog.

According to a preferred embodiment of the present invention, implant analog 10 is provided with at least two retention members. The retention members provide for suitably securing the location and the rotational angle measured relative to an axis of rotation that is perpendicular to the axis of the improved implant analog after being introduced into the physical model of the mouth of a patient, not shown. These retention members also provide for respectively snap locking and/or snap releasing the implant analog within, or off, a dedicated receiving bore that is structured in the body of the physical model. Namely these retention members are also used as means for fast connecting/releasing the implant analog, to, or off, the physical model. Connecting an improved implant analog of the invention to a physical model is accomplished by introducing the bottom of the improved implant analog into a respective receiving bore and pushing the implant analog inwards down to the point in which a "click" is sounded or at least felt by touching. Releasing the implant analog off the physical model is accomplished by pulling it out of the receiving bore. Circumferential groove 18 provides for housing one of these retention members which is an O-ring, not shown. This O-ring is made of a resilient material, such as silicon rubber, or Polyether ether ketone (PEEK). This O-ring mainly provides for centering the upper segment of the improved implant analog, such that the axis of the implant analog coincides with the axis of the receiving bore that is structured in the body of the physical model. The friction generated between the O-ring and the surface of the receiving bore provides for fixing the improved implant analog in its place within the receiving bore. A spherical male fitting implements retention member 26. It fits in dimensions and geometrical shape with a respective spherical female fitting, which is suitably placed and enclosed within a niche structured at the end of the receiving bore which is adjacent to the base of the physical model. Both of these at least two retention members—the O-ring placed within groove 18 and retention member 26 provide for securing implant analog 10 fixed within the physical model. Any common snap locking mechanism that is locked by pushing and released off by pulling can be employed for fast connecting/releasing and securing the improved implant analog onto the physical model according to the method of the present invention. Exemplary is a snap locking mechanism which comprises a stiff ball that is resiliently attached to a side surface of the body of the implant analog, such that it can reciprocally move back and forth in a perpendicular direction to this surface; and a matching recess structured at a side surface of the receiving bore.

One or more directional members axially disposed across a surface of the improved implant analog provide according to the method of the present invention for suitably orienting the improved implant analog when it is installed within the receiving bore of the physical model. Planar contours, which are longitudinally disposed across the surface of the body of improved implant analog 10, such as contours 20, provide for suitably guiding and axially orienting implant analog 10 at the suitable and predefined rotational angle relative to its axis, when it is placed within the respective receiving bore of the physical model considered. Optional axial grooves such as an elongated groove 24 axially disposed across a surface of the improved implant analog, or an elongated axial ridge, serve for the same guiding and orienting purposes. A circumferential keying polygon, such as pentagon 16 is less favorable for axially orienting the improved implant analog because the polygon may comply with more than one rotational angle. Nevertheless, such keying polygon can be used as a directional member according to the present invention.

A passageway connects between the lumen of bore 12 its surface is threaded as described hereinabove, and aperture 32 which is disposed at the bottom of retention member 26. This passageway provides for releasing excessive pressure when a replica of the abutment is casted, in cases in which the lumen of the implant analog is used as a mold for such casting. The body of an implant analog in accordance with a preferred embodiment of the present invention is made of polished stainless steel, or a hard metal such as titanium. Improved implant analogs their bodies are made of stiff plastic resin, and or common dental composite materials are in accordance of the present invention.

In FIGS. 2A-2B two elevational views of the female fitting 40 of retention member 26 are respectively shown. The body of female fitting 40 is made of resilient material. Therefore this female fitting provides for snap engaging the spherical retention member 26 of implant analog 10 described above. Female fitting 40 is a spherical recess structured in cube 41 that can be removably attached to the body of the physical model. Alternatively such spherical recess is structured within a cylinder that is structured and arranged to be installed at the end of the receiving bore that is adjacent to the base of the physical model. Aperture 42 is disposed at a plane located at a predefined level above the base of the physical model considered. In cases that retention member 26 is engaged with its spherical female fitting 40 it provides for supporting the implant analog at the desired and predefined height measured relative to the impression of the gum and for strengthening the connection between the implant analog and the body of the physical model. Such support and mechanical strengthening are required when the technician processes by say, milling, the abutment for its customization; or when the technician presses it in the course of processing of the respective dental prosthesis. Female fitting 40 provides for fixing the face of implant analog 10 at the suitable level above the base of the physical model considered. The dimensions and geometrical shape of the body of retention member 26 fit in with the dimensions and shape of the respective female fitting 40. The radius of circular aperture 42, which is the aperture of the spherical niche that is centrally disposed at the upper face of female fitting 40, is somewhat smaller compared to the radius of the male spherical retention member of the implant analog considered. However the radius of the spherical niche closely fits in with the radius of the spherical retention member 26. Therefore whenever the implant analog is forced towards the base of the physical model spherical retention member 26 snap engages the respective niche with a "klick". Pulling the implant analog in the opposite direction frees the spherical retention member off the spherical niche. Female fitting 40 is made of resilient material such as nylon or polyether ether ketone (PEEK).

The shape and dimensions of a customized abutment is derived in accordance with the relevant clinical data of a patient (e.g., teeth, edentulous ridges, gums and especially the first impression of the gum that is taken after the gum and bone at the periphery of the implant has fully recovered) as known. For customizing, a common abutment is first mounted onto the improved implant analog. The implant analog including the abutment installed therein is mounted and secured onto the physical model. The connection between the abutment and the implant analog is secured by screwing at a predefined level of rotational torque, as known. Such mounting is accomplished prior to the initiation of the processing of the abutment, such as by milling. At the end of the processing the customized abutment can be fixed firmly within the implant. Then the customized abutment, following its mounting onto the implant, is first used for carrying for example a temporary crown.

Prior to the introduction of the customized abutment and firmly securing it into the implant the technician casts according to the method of the present invention a replica of the abutment. Such casting is accomplished according to a preferred embodiment of the method of the present invention by employing a mold which comprises the improved implant analog as well as the negative impression of the segment of the abutment which protrudes off the implant analog. Materials normally utilized for such casting may include according to the method of the present invention dental composite materials commonly used in dentistry as restorative materials or adhesives. From the moment in which the casting of the replica of the custom abutment has been accomplished, the implant analog is firmly connected to the replica of the abutment. Contrary to the situation in which a customized abutment can be easily removed off the improved implant analog by screwing, the rest of the casted body of the replica of the customized abutment that is enclosed within the improved implant analog can be hardly removed. From the moment in which the curing of the casted replica is accomplished on, the implant analog from which a segment of the replica of the abutment protrudes can be removed off the physical model and replaced back into the physical model again and again, as the technician wishes. Nevertheless, during the entire process in the course of the preparation of the final dental prosthesis, the respective customized abutment remains securely connected to the implant, which is located within the mouth of the patient.

In cases in which the replica of the custom abutment accidentally breaks off, the technician attaches the fragments with glue to restore the replica back by using pentagon 16 that is located close to the face of the implant analog for suitably orienting the external segment of the refurbished replica relative to the axis of the implant analog.

Figure 3:
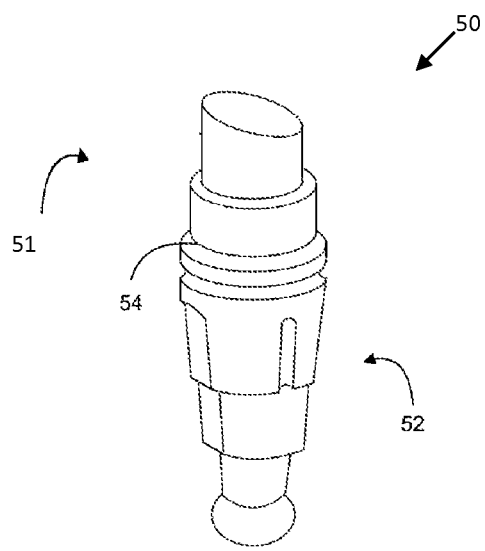
FIG. 3 is a schematic view of an exemplary replica of the invention.

FIG. 3 shows a schematic view of replica 50 of a custom abutment according to a preferred embodiment of the present invention. Segment 51 of the replica of the custom abutment protrudes off improved implant analog 52. Edge 54 is the end of fully exposed segment 51 that protrudes off body 52 of the improved implant analog. A partial segment of segment 51 one end of which is edge 54 encloses the pentagon described hereinabove. The rest of the body of the casted replica of the abutment considered, not shown, is fully enclosed within the lumen of body 52 of the improved implant analog. The rest of the body of the replica is referred hereinafter as the internal segment of the replica of the custom abutment.

Alternatively, an integral unit of the replica of the improved implant analog out of which a segment of the customized abutment protrudes is casted according to another preferred embodiment of the method of the present invention. This integral unit is referred hereinafter as the replica according to the second preferred embodiment. This casted unit substitutes the replica of the abutment that is casted into the lumen of the implant analog according to the first embodiment of the method of the present invention described above. The integral unit is employed in accordance with this second preferred embodiment of the present invention for supporting the very dental prosthesis in the course of its preparation. Namely, the replica according to the second embodiment of the method of the present invention includes segment 51 as well as body 52. Both of these two segments are integrally connected to each other and both of them are made of the same material. The dental prosthesis is attached to the physical model of the mouth of the patient for its evaluation following each accomplished step in the process of its preparation, as known. Such attaching is accomplished by means of a casted replica according to any of these two preferred embodiments of the method of the present invention described above.

What is claimed is:

1. A method of preparing a dental prosthesis to be installed onto a dental implant by means of a customized abutment, wherein said dental prosthesis is removably attached during said preparing to a physical model of a patient's mouth by means of a replica of said abutment and said replica comprises a shape of a segment of said customized abutment, said method comprising:

i. mounting a common abutment onto an implant analog;
   ii. connecting said implant analog to a respective receiving bore included in said physical model;
   iii. processing said common abutment to form said customized abutment;
   iv. preparing a mold comprising said implant analog and a negative impression of at least a segment of said customized abutment;
   v. removing said customized abutment from said implant analog;
   vi. securing said customized abutment into said dental implant in a patient mouth;
   vii. casting said replica by means of said mold;
   viii. attaching said dental prosthesis onto said physical model by means of said casted replica for evaluation while preparing said dental prosthesis;
   ix. removing said prepared prosthesis from said replica; and
   x. attaching said dental prosthesis to said customized abutment in the patient's mouth.

2. The method as in claim 1, and wherein said implant analog comprises at least one directional member, and wherein said at least one directional member is selected from a group of directional members consisting of a planar contour axially disposed across a surface of said implant analog, an elongated grove axially disposed across a surface of said implant analog, an elongated ridge axially disposed across a surface of said implant analog, a keying polygon circumferentially disposed across a surface of said implant analog, and any combination thereof.

3. The method as in claim 1, wherein said casting is accomplished by means of a mold which comprises a segment of a lumen of said implant analog.

4. The method as in claim 1, wherein said casted replica further comprises a replica of a segment of the body of said implant analog.

* * * * *